(12) United States Patent
Siess et al.

(10) Patent No.: US 11,107,626 B2
(45) Date of Patent: Aug. 31, 2021

(54) INTRAVASCULAR BLOOD PUMP COMPRISING CORROSION RESISTANT PERMANENT MAGNET

(71) Applicant: Abiomed Europe GmbH, Aachen (DE)

(72) Inventors: Thorsten Siess, Aachen (DE); Claudia Mourran, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 0 days.

(21) Appl. No.: 16/346,198

(22) PCT Filed: Oct. 25, 2017

(86) PCT No.: PCT/EP2017/077334
§ 371 (c)(1),
(2) Date: Apr. 30, 2019

(87) PCT Pub. No.: WO2018/082987
PCT Pub. Date: May 11, 2018

(65) Prior Publication Data
US 2019/0311850 A1   Oct. 10, 2019

(30) Foreign Application Priority Data

Nov. 2, 2016   (EP) ..................................... 16196804

(51) Int. Cl.
| | |
|---|---|
| *A61M 60/135* | (2021.01) |
| *H01F 41/02* | (2006.01) |
| *H01F 7/02* | (2006.01) |
| *A61M 60/82* | (2021.01) |
| *A61M 60/419* | (2021.01) |

(Continued)

(52) U.S. Cl.
CPC ......... *H01F 41/026* (2013.01); *A61M 60/135* (2021.01); *A61M 60/419* (2021.01); *A61M 60/422* (2021.01); *A61M 60/82* (2021.01); *H01F 7/02* (2013.01); *H01F 7/0221* (2013.01);

(Continued)

(58) Field of Classification Search
CPC .............. A61M 1/1015; A61M 1/1031; A61M 1/1036; A61M 1/125; A61M 60/135; A61M 60/205; A61M 60/419; A61M 60/422; A61M 60/818; A61M 60/82;

(Continued)

(56) References Cited

U.S. PATENT DOCUMENTS

| | | | |
|---|---|---|---|
| 2003/0041920 A1 | 3/2003 | Hoshi et al. | |
| 2008/0200750 A1 | 8/2008 | James | |
| 2016/0088756 A1* | 3/2016 | Ramadas | ............ H01L 51/5259 361/728 |

FOREIGN PATENT DOCUMENTS

WO   2016118735 A1   7/2016

OTHER PUBLICATIONS

International Search Report and Written Opinion for Application No. PCT/EP2017/077334 dated Feb. 2, 2018.

* cited by examiner

*Primary Examiner* — George Manuel
(74) *Attorney, Agent, or Firm* — Botos Churchill IP Law LLP

(57) ABSTRACT

This invention is directed to a corrosion resistant permanent magnet, to a method for producing a corrosion resistant permanent magnet, and to an intravascular blood pump comprising the magnet. The magnet is corrosion resistant due to a composite coating comprising a metal layer, optionally a metal oxide layer, a layer formed from poly(2-chloro-p-xylylene), and a linker layer between the metal oxide layer and the poly(2-chloro-p-xylylene) layer.

Figure 1:
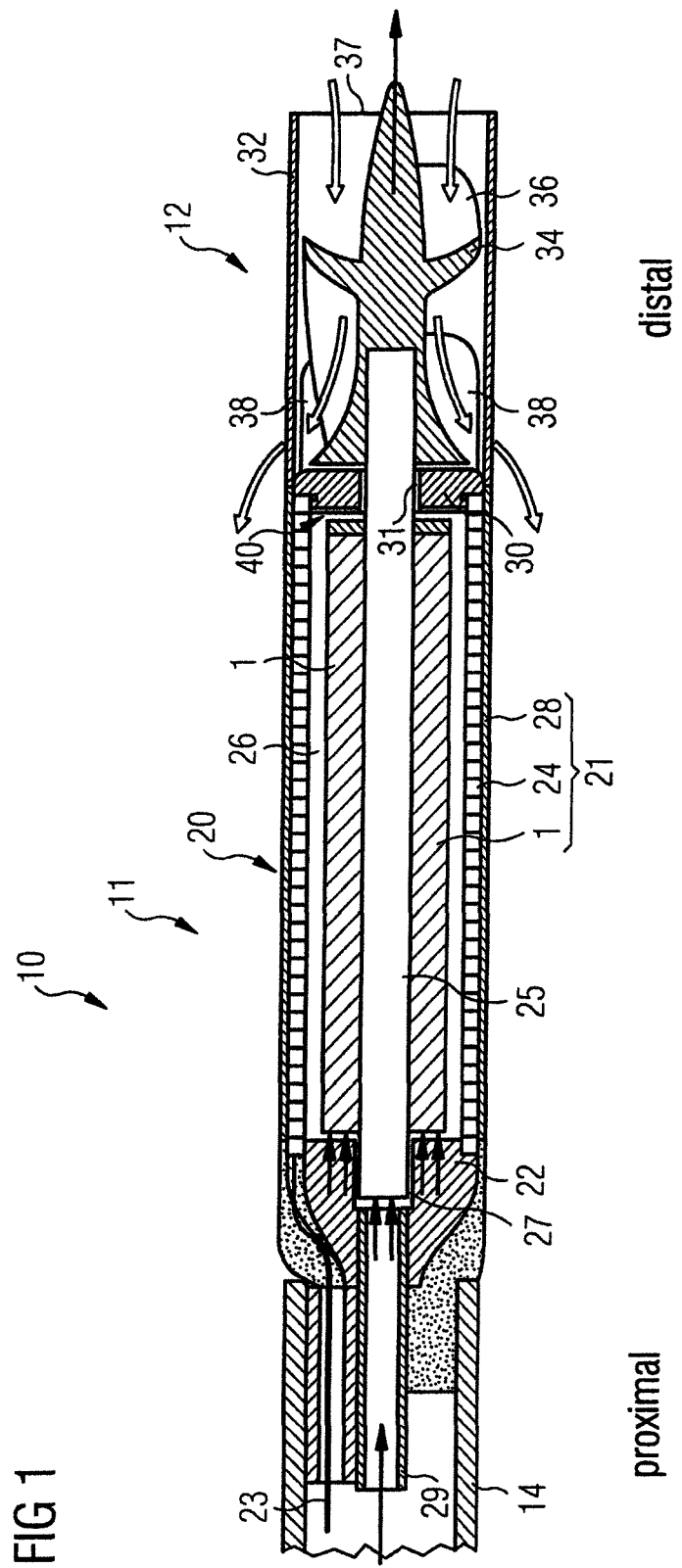

40 Claims, 2 Drawing Sheets proximal                                                                                          distal

(51) Int. Cl.
*A61M 60/422* (2021.01)
*H01F 1/055* (2006.01)
*H01F 1/057* (2006.01)

(52) U.S. Cl.
CPC .......... *F16C 2316/18* (2013.01); *H01F 1/057* (2013.01); *H01F 1/0557* (2013.01)

(58) Field of Classification Search
CPC ........................ A61M 60/829; F16C 2316/18; H01F 1/0557; H01F 1/057; H01F 41/026; H01F 7/02; H01F 7/0221
See application file for complete search history.

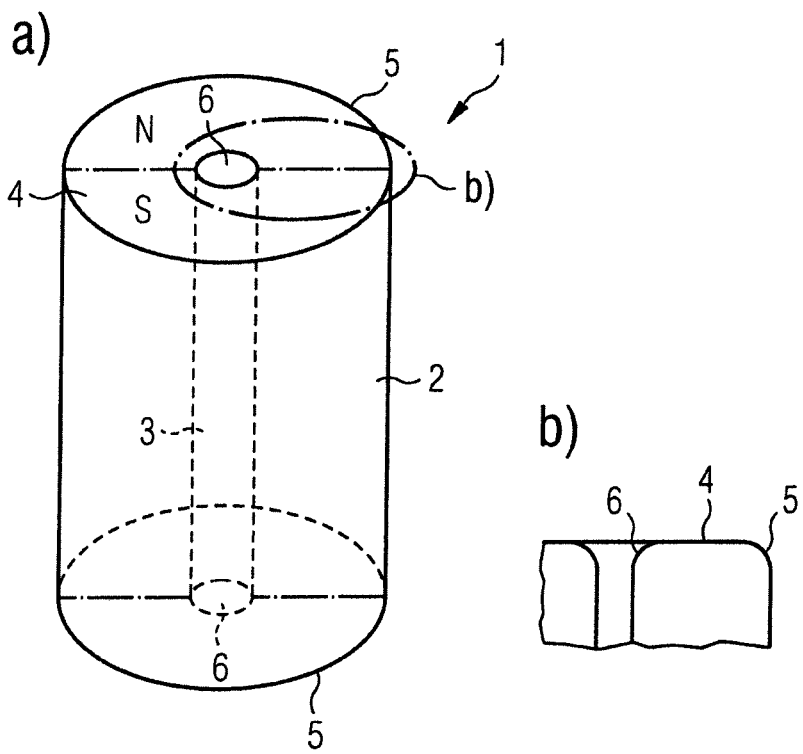

INTRAVASCULAR BLOOD PUMP COMPRISING CORROSION RESISTANT PERMANENT MAGNET

CROSS-REFERENCE TO RELATED APPLICATIONS

This application is a United States National Stage filing under 35 U.S.C. § 371 of International Application No. PCT/EP2017/077334, filed Oct. 25, 2017, which claims the benefit of European Patent Application No. 16196804.5, filed Nov. 2, 2016 the contents of all of which are incorporated by reference herein in their entirety. International Application No. PCT/EP2017/077334 was published under PCT Article 21(2) in English.

This invention relates to corrosion protection of permanent magnets. In particular, this invention relates to permanent magnets having a protective coating rendering the magnets resistant to corrosion, and to methods for producing corrosion resistant permanent magnets. This invention also relates to intravascular blood pumps comprising the inventive corrosion resistant permanent magnets. While the invention is applicable to all kinds of permanent magnets, rare earth permanent magnets are preferred, and neodymium iron boron (NdFeB) permanent magnets are particularly preferred.

Intravascular blood pumps support blood flow in a patient's blood vessel. They are inserted percutaneously into, for example, the femoral artery and guided through the body's vascular system to their destination, for example a ventricle of the heart.

A blood pump typically comprises a pump casing having a blood flow inlet and a blood flow outlet. In order to cause a blood flow from the blood flow inlet to the blood flow outlet, an impeller or rotor is rotatably supported within the pump casing about an axis of rotation, with the impeller being provided with one or more blades for conveying blood.

An exemplary blood pump is illustrated in FIG. 1. FIG. 1 is a schematic longitudinal section of an exemplary intravascular blood pump 10. The blood pump has a motor section 11 and a pump section 12 which are disposed coaxially one behind the other and result in a rod-shaped construction form. The pump section is extended by a flexible suction hose (not shown) which has, at its end and/or in its side wall, openings for the entry of blood to the pump. The end of the blood pump 10 facing away from the suction hose is connected to a catheter 14, optionally in combination with a guide wire for steering the blood pump to its destination.

The exemplary intravascular blood pump shown in FIG. 1 has the motor section 11 and the pump section 12 firmly connected to one another. The motor section 11 has an elongate housing 20 in which the electric motor 21 is housed. An electric motor has a rotor and a stator. The stator is the stationary part of the motor's electromagnetic circuit, while the rotor is the moving part. Either the rotor or the stator comprises electrically conductive windings, while the other one comprises permanent magnets. Electrical current flowing in the windings creates an electromagnetic field interacting with the magnetic field of the permanent magnets to generate the forces that turn the rotor. In the exemplary blood pump of FIG. 1, the stator 24 of the electric motor 21 has, in the usual way, numerous circumferentially distributed windings as well as a magnetic return path 28 in the longitudinal direction. It is firmly connected to the motor housing. The stator 24 surrounds the rotor 1 connected to the motor shaft 25 and consisting of a permanent magnet magnetized in the active direction. The motor shaft 25 extends over the total length of the motor housing 20 and protrudes distally out of the latter. There, it carries an impeller 34 with blades 36 projecting therefrom or pump blades which rotate within a tubular pump housing 32 which is in turn firmly connected to the motor housing 20.

The proximal end of the motor housing 20 has the flexible catheter 14 sealingly attached thereto. In the present disclosure "proximal" and "distal" indicate the position with respect to a physician inserting the intravascular blood pump, i.e. the distal end is at the impeller side. Through the catheter 14 there extend electrical cables 23 for power supply to and control of the electric motor 21. There additionally extends through the catheter 14 a purge-fluid line 29 which penetrates the proximal end wall 22 of the motor housing 20. Purge fluid (schematically illustrated by bold arrows) is fed through the purge-fluid line 29 into the interior of the motor housing 20, flows through clearance 26 between the rotor 1 and the stator 24, and exits through the end face 30 at the distal end of the motor housing. The purging pressure is so chosen that it is higher than the blood pressure present, in order to thereby prevent blood from penetrating into the motor housing. Depending on the case of application, the pressure of the purge fluid is between 300 and 1400 mmHg at the motor where the pressure is built up.

Well suited as a purge fluid is a fluid having a viscosity higher than the viscosity of water (q=0.75 mPa·s at 37° C.), in particular a purge fluid having a viscosity at 37° C. of 1.2 mPa·s or higher. For example, a solution of 5% to 40% glucose in water for injection can be used, but physiological saline solution is also suitable.

Upon rotation of the impeller 34, blood (schematically illustrated by unfilled arrows) is sucked through the end-face suction opening 37 of the pump housing 32 and conveyed backward within the pump housing 32 in the axial direction. Through outlet openings 38 of the pump housing 32 the blood flows out of the pump section 12 and further along the motor housing 20. It is also possible to operate the pump section with the reverse conveying direction, with the blood being sucked in along the motor housing 20 and exiting from the opening 37.

The motor shaft 25 is mounted in radial bearings 27 and 31 at the proximal end of the motor housing, on the one hand, and at the distal end of the motor housing, on the other hand. Furthermore, the motor shaft 25 is also mounted axially in an axial bearing 40. Should the blood pump be used for conveying blood also or only in the reverse direction, a corresponding axial bearing 40 is also/only provided at the proximal end of the motor housing 20 in a corresponding manner.

It is stressed that the blood pump described above is just an example, the present invention also being applicable to different blood pumps comprising an electric motor, i.e. requiring permanent magnets.

Intravascular blood pumps must meet numerous requirements. Due to their placement within a living body they should be as small as possible. The smallest pumps presently in use have an outer diameter of about 4 mm. Nevertheless, the pumps must convey high volume flows in human blood circulation. Therefore, the minute pumps have to be high-performance engines.

Furthermore, the implantable blood pumps must not detrimentally influence their biological environment such as the blood to be pumped and the surrounding tissue. Therefore, the pumps should be biocompatible in a broad sense, i.e.

they should not contain or produce any potentially noxious materials or considerable heat that might damage the body or constituents thereof.

In addition, replacement of a pump is burdensome to the patient. It follows from his, and of course also from financial considerations, that intravascular blood pumps should have a long useful life, desirably 180 days or longer.

Materials and design of the intravascular blood pumps must be appropriately selected and specifically adapted to meet these various requirements.

Importantly, an appropriate permanent magnet for the electric motor must be selected. With a view to efficiency and longevity of the pump, the magnet should have a strong magnetic field, i.e. high remanence, high resistance to demagnetization, i.e. high coercivity, and a high saturation magnetization. In this respect, rare earth permanent magnets, in particular those having neodymium as the rare earth metal, and especially neodymium iron boron (NdFeB) permanent magnets, are the magnets of choice. Other rare earth iron boron permanent magnets may also be used.

The stronger the magnet, the smaller the magnet can be while still generating sufficient rotational force. Thus, the stronger the magnet, the smaller the electric motor can be. NdFeB permanent magnets are the strongest permanent magnets currently available. They seem to be ideal for use in intravascular blood pumps.

It is well-known that the magnetic properties of rare earth metal based magnets, for example of NdFeB magnets, depend on the particular alloy composition, microstructure, and the manufacturing techniques employed. NdFeB magnets are available as polymer bonded magnets and as sintered magnets. Sintered magnets are superior in magnetic properties. They are prepared by alloying the raw materials, grinding to powder, pressing and sintering. During or after preparation, an external magnetic field is applied in order to magnetize the material. A well-studied magnet is a fine-crystalline sintered material wherein $Nd_2Fe_{14}B$ crystals are surrounded by a thin layer particularly rich in neodymium.

While neodymium iron boron magnets have magnetic properties rendering them particularly suitable for use in electric motors of intravascular blood pumps, they also have a serious disadvantage. Namely, commercially available NdFeB magnets, which consist mainly of neodymium, iron and boron, and in particular the sintered neodymium iron boron magnets which have a very active neodymium rich phase at the grain boundaries, are very vulnerable to corrosion. The magnets may be, for example, corroded by oxygen and moisture in air, in particular, but not only, at grain boundaries. The corrosion leads to a profound decrease in the magnetic properties, and if the corrosion progresses while the magnet is in use, the performance of the blood pump using the magnet deteriorates. The phenomenon is exacerbated by the tendency of neodymium iron boron magnets to act as a sponge for corrosion products, breaking the structure and leading to spalling off of pieces from the surface of the magnet and finally to crumbling of the magnet.

Unfortunately, liability to corrosion is a property which is common to all rare earth metals. Therefore, all rare earth metal based permanent magnets have an unfavorable tendency to corrode, as explained for NdFeB magnets above. For currently available magnets it can be said, as a rule of thumb, that the stronger the magnet, the greater its liability to corrosion.

In an intravascular blood pump, the magnets have to work in a corrosive environment, namely, in the purging liquid flowing between the rotor and the stator (see FIG. 1). As described above, the purge fluid is typically an aqueous fluid, possibly a fluid containing chloride. Chloride is highly corrosive for rare earth metal based magnets, but also water and oxygen dissolved in the water cause severe corrosion within very short time spans of only a few hours.

Clearly, rare earth metal based permanent magnets, such as neodymium iron boron magnets, for intravascular blood pumps need to be protected against corrosion.

Various measures for protecting neodymium iron boron magnets and other rare earth metal based magnets against corrosion are known. For example, corrosion resistance may be improved by coating the magnets with protective coatings.

Usual coatings are nickel coatings and coatings based on epoxy resins, and, especially for blood pumps, titanium coatings and Parylene coatings are known. These coatings, however, also have disadvantages. Even if biocompatible metals and organic resins are respectively selected, such as titanium and Parylene, there is the problem that metal coatings must be relatively thick in order to provide sufficient protection. As a result, the gap between the magnet and the windings in the electric motor of the blood pump must be relatively large. A large gap has a strong negative effect on the performance of the electric motor. A large gap demands a higher motor current, and high motor currents produce undesirable heat which may lead to damage of blood and tissue.

Further, organic materials such as Parylene have thermal expansion coefficients which are considerably different from the thermal expansion coefficient of the magnet. Therefore, temperature variations during use of the magnet often lead to cracking and/or delamination of the coating.

At present, no biocompatible coating for permanent magnets, e.g. neodymium iron boron magnets, is known to fulfil all the requirements for use in an intravascular blood pump. Such a coating must be excellent in corrosion resistance itself, must be thin but nevertheless dense, must not develop cracks or other defects during use, and must reliably and closely adhere to the magnet. Of course, the coating must be biocompatible, and it must coat with uniform thickness either the complete magnet or at least those portions of the magnet which are exposed to a corrosive environment during use of the magnet. This is particularly demanding because many magnets have a porous surface and a shape comprising edges. Therefore, permanent magnets such as rare earth metal based magnets, e.g. neodymium iron boron magnets, for use in intravascular blood pumps constitute items which cannot be coated easily with a uniform thickness.

The present invention provides a solution to the problems described above.

The present invention provides a coating for permanent magnets which reliably protects the magnets against corrosion while in use in an intravascular blood pump over an extended period of time.

The subject-matter of the present invention involves a corrosion resistant permanent magnet having the features recited in independent claim 1, a method for producing a corrosion resistant permanent magnet, the method having the features recited in independent claim 21, and an intravascular blood pump having the features recited in independent claim 30. Embodiments of the invention are disclosed in the respective dependent claims.

A magnet is corrosion resistant in the sense of this invention if it passes the test described in the experimental section.

According to the present invention, a strong permanent magnet comprises a coating either completely surrounding a magnet body or covering at least those surfaces of the magnet body which are exposed to fluid when the magnet is operating in an intravascular blood pump. The coating renders the magnet resistant to corrosion while in use in an intravascular blood pump. Preferred magnet bodies are sintered magnets consisting primarily of neodymium, iron, and boron, with fine tetragonal magnetic $Nd_2Fe_{14}B$ crystals and a neodymium rich non-magnetic phase surrounding the crystals, as described above. Typically, the $Nd_2Fe_{14}B$ crystals forming the main phase have a mean crystal diameter within a range of 1 to 80 μm. The non-magnetic neodymium rich phase makes up from 1% to 50% by volume of the magnet body. These magnets are readily available commercially. They are preferred because they have high magnetic characteristics, and because they are particularly strong, i.e. have a high flux density. For the reasons indicated above, an application in intravascular blood pumps requires particularly strong magnets. In principle, however, the inventive corrosion resistant coating can be applied to any material requiring protection against corrosion, for example different rare earth iron boron magnetic materials or any other magnetic materials.

The inventive coating is a composite coating provided on surfaces of the magnet body, i.e. the actual magnetic material. The composite coating comprises a metal layer on surfaces of the magnet body, optionally a metal oxide layer on the metal layer at the exposed surfaces thereof, a layer formed from poly(2-chloro-pxylylene), and a linker layer between the metal layer or the metal oxide layer and the poly(2-chloro-p-xylylene) layer.

Rare earth metal based magnets as purchased from a supplier are typically protected by a phosphate coating. This phosphate coating may be removed, for example by washing with an acid, prior to application of the metal layer. However, the phosphate coating does not detrimentally interfere with the coating or the coating process according to the present invention and may, therefore, remain on the magnet body. Preferably, the phosphate coating is not removed. Not removing the phosphate coating saves one process step and avoids introduction of impurities during such process step. It is, however, preferable to clean the magnet prior to application of the metal layer. Cleaning is preferably performed by washing the magnet with an organic solvent, for example an alcohol. Particularly preferred cleaning agents are isopropanol and a mixture of isopropanol and ethanol. After washing with an organic solvent, the magnet is dried, for example in vacuum or in an air stream.

After cleaning and drying, the metal layer is applied to the surface of the magnet body. The metal for forming the metal layer is not particularly restricted. The term "metal" as used herein must be understood as including metal alloys. Suitable for forming the metal layer are any metals (metal alloys) which can form a dense layer and are biocompatible. Likewise, the method for applying the metal layer is not particularly limited. Exemplary application methods include dry methods such as physical vapor deposition, in particular ion vapor deposition, plasma coating and atomic layer deposition, and wet methods such as galvanic deposition (ion plating). Plasma deposition and ion vapor deposition are quite fast and cost effective methods, but it appears that wet deposition yields metal layers having a better quality, i.e. metal layers having an enhanced density. However, layers deposited by ion vapor deposition or other dry methods have superior long term stability.

The preferred metal for forming the metal layer is aluminum. Galvanic deposition of aluminum is performed out of ionic liquids in a manner usual in the art, for example by using a mixture of aluminum chloride and 1-ethyl-3-methylimidazoliumchloride. The aluminum is preferably pure, e.g. at least 99% pure, and particularly preferably at least 99.9% pure.

Aluminum forms a passivating oxide layer when exposed to air. This naturally formed (native) oxide layer is only a few nanometers thin and adheres well to the underlying metal. Other metals forming a native oxide layer are also suitable. Exemplary metals include titanium, tantalum, niobium, zirconium and alloys of two or more of these metals, e.g. aluminum alloy and niobium titanium alloy. In the present invention, oxide layers are formed by oxidation of the metal coated on the magnet body either automatically upon exposure to air or artificially, e.g. by anodic oxidation. In any case, the oxide layer is only a few nanometers thick, e.g. about 2 to 5 nanometers. However, the invention also works well without an oxide layer, and biocompatible metals without an oxide layer may be advantageously used. Such metals and metal alloys are, for example, noble metals, e.g. platinum and gold.

The thickness of the metal layer, and of the combined metal/metal oxide layer, is preferably small, i.e. about 20 μm or less. A thickness of 10 μm or less is particularly preferred.

In order to enhance the corrosion protection provided by the metal layer or the metal/metal oxide layer, the metal layer or the metal/metal oxide layer is combined with a poly(p-xylylene)polymer layer. Poly(p-xylylene)polymers are known under the trade name Parylene. Parylenes may react with hydroxyl group containing surfaces, and are known to form pin-hole free coatings at low layer thicknesses. In addition, they have low dielectric constants (about 3), which is advantageous in implantable blood pumps. A composite coating comprising a metal layer or a metal/metal oxide layer and a Parylene layer is biocompatible and also provides corrosion protection. However, the adhesion of the Parylene layer to the metal layer or the metal oxide layer is not sufficiently strong under the working conditions in an intravascular blood pump. The Parylene layer starts to delaminate after an unacceptably short time, thus exposing the metal or metal oxide layer. The metal layer or the metal/metal oxide layer cannot sufficiently protect the magnet body, and thus corrosion of the magnet body sets in.

According to the present invention, this scenario is prevented by a combination of two measures: provision of an interface layer linking the metal layer or the metal oxide layer and the Parylene layer, and use of a particular Parylene compound.

The compound forming the interface layer, i.e. the linker compound, must be bifunctional. Bifunctional means that the linker compound must have two types of functional groups or molecular moieties of different functionality (reactivity), one functional group or molecular moiety bonding to the metal layer or the metal oxide layer, e.g. by reacting with surface hydroxyl groups of the metal or metal oxide layer, and the other functional group or molecular moiety bonding to Parylene, thus firmly linking the inorganic metal layer or metal oxide layer and the organic Parylene layer. Linking may be provided by covalent bonds or other bonds, e.g. by van der Waals forces.

Linkers having functional groups or moieties bonding to metals or metal oxides, and functional groups or moieties bonding to Parylene, are known. As exemplary linkers, mention may be made of silane compounds, mercaptans, phosphines, disulfides, and silanes having a thiol, phosphine or disulfide group. Depending on the metal, different linker compounds are preferred.

In the case of aluminum, titanium, tantalum, niobium, zirconium, and oxides of these metals, linkers for the metal layers and for the metal oxide layers are preferably alkoxysilanes, such as methoxysilanes and ethoxysilanes, for example silanes having the formula $(H_3CO)_3Si$—R, with R being e.g. methacrylate, alkylamine, phenylamine, or epoxyalkyl. For bonding to Parylene, the linkers preferably have an acryloyloxy or methacryloyloxy functional group. The carbon chain length between the silyl portion and the (meth)acryloyloxy portion of the linker typically has from 1 to 16 carbon atoms (methyl, ethyl, propyl, butyl, pentyl . . . ). The hydrocarbon chain is typically saturated, but may also contain one or more unsaturated bonds. A particularly preferred linker is 3-(trimethoxysilyl)propyl methacrylate (A-174) from Silquest, but other silane compounds such as G-170 from Silquest (a vinylfunctional silane coupling agent) are also suitable. In addition, linkers having bistrimethoxysilyl or bis-triethoxysilyl functionalities may be used, for example bis(trimethoxysilylethyl) benzene.

In particular for titanium, zirconium and platinum, linkers having hydrid-functional groups such as trihydrosilanes work well. 10-undecenylsilane and noctadecylsilane may be specifically mentioned. The silanes are preferably applied at room temperature from the vapor phase or from an aprotic solution. In addition, the above-mentioned alkoxysilanes having (meth)acryloyloxy groups, and the compounds having bis-trimethoxysilyl or bis-triethoxysilyl functionalities, are also suitable.

Linkers suitable for linking the Parylene layer to a gold layer are typically mercaptans, phosphines or disulfides, preferably with longer hydrocarbon chains, such as alkyl- or dialkyl-disulfides with alkyl groups having from 10 to 16 carbon atoms. Such alkyl groups form dense and well ordered layers on the metal or metal oxide surface. However, alkyl groups having only from 1 to 9 carbon atoms may also be used.

Equally appropriate for gold layers are silane linker compounds having thiol, phosphine or disulfide groups. Particularly preferred examples are 3-(2-pyridylethyl)thiopropyl trimethoxysilane, 3-(4-pyridylethyl)thiopropyl trimethoxysilane, 2-(diphenylphosphino)ethyl triethoxysilane, bis(2-methacryloyl)oxyethyldisulfide, and dihexadecyldisulfide.

The bifunctional linkers are preferably applied to the metal or metal oxide surface by a plasma coating process or by physical vapor deposition without plasma or by applying an aprotic, or an alcoholic or an aqueous solution of the bifunctional linker compound to the metal surface or the metal oxide surface. Dry coating of silane compounds in a plasma chamber yields glassy layers comprising Si—O—Si—O— chains arranged substantially parallel to the metal oxide surface and bonded to the surface via oxygen atoms. An organic residue faces away from the surface and is available for bonding to the Parylene. Physical vapor deposition and wet application form interface layers having a similar structure, but without a glassy appearance.

Plasma deposition yields a dense layer with acceptable adherence to Parylene. Physical vapor deposition without plasma yields less dense layers having better adherence to Parylenes than plasma deposited layers. Wet application yields very dense monolayers having an irregular network and a high degree of crosslinking and a high percentage of silicon-bonded oxygen. These layers also adhere very well to Parylene layers. Therefore, wet application is particularly preferable.

Alternatively, plasma application and physical vapor deposition (without plasma) or wet application processes can be combined, i.e. a glassy interface layer is first formed by plasma deposition, followed by physical vapor deposition or wet application of a second linker layer, thus forming a composite linker layer. In such composite linker layer, silicon atoms of the glassy layer are linked covalently to oxygen atoms of the second layer, with organic residues (such as methacrylate, alkylamine, or epoxyalkyl) of the second layer being available for bonding the Parylenes, either covalently or in a different manner, e.g. by van der Waals forces.

The interface layer typically has a thickness in the range from 20 to 150 nm, preferably from 50 to 100 nm.

Finally, a Parylene layer, i.e. a poly(p-xylylene)polymer layer, is formed on the interface layer. Poly(p-xylylene) polymers have the structural formula

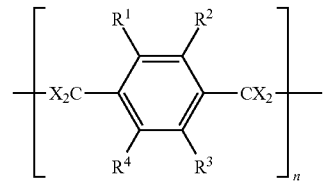

wherein n is the polymerization degree.

Precursors of poly(p-xylylene) compounds are [2.2]paracyclophanes having the structural formula

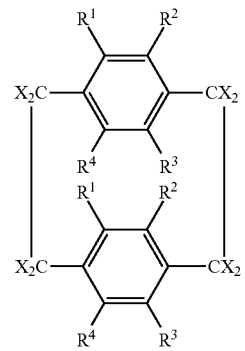

The dimeric compounds are available on the market, for example precursors of Parylene N, Parylene C, Parylene D, and Parylene F. In Parylene N, all of X and R1 to R4 are hydrogen, in Parylene C, one of R1 to R4 is chlorine while the other residues R as well as X are hydrogen, in Parylene D, two of the residues R1 to R4 are chlorine while all other residues are hydrogen, and in Parylene F, the residues X are fluorine while the residues R1 to R4 are hydrogen. Parylene layers are typically used as moisture barriers and dielectric barriers.

At high temperatures (above about 500° C., depending on the particular Parylene) under vacuum, the dimers are cracked to form the corresponding p-xylylene radicals. The monomers polymerize to form poly(p-xylylene) polymers, on the one hand, and bond to the interface layer via the functional groups thereof, e.g. methacrylate groups, on the other hand. Alternatively, they may simply adhere to hydrophobic portions of the interface layer.

According to this invention, it has been found that Parylene C, wherein one of R1 to R4 is chlorine, forms a coating rendering magnetic materials resistant to corrosion under the conditions encountered in intravascular blood pumps, when applied as the cover layer of the composite layer described above. The Parylene C layer is preferably applied by plasma deposition, and the layer thickness is preferably in a range from 5 to 20 µm, more preferably from 10 to 16 µm.

When Parylene C is applied directly onto the surface of the magnetic material, crack formation and delamination of the protective Parylene C layer and corrosion of the magnetic material are observed within a few days. Likewise, if Parylene C is applied onto a metal layer or a metal/metal oxide layer, corrosion of the magnetic material is observed under the conditions in an intravascular blood pump within an unacceptably short time period, due to delamination. In addition, Parylene compounds different from Parylene C do not provide sufficient corrosion protection, even if an adhesion promoter is used, e.g. if applied on a silane based interface layer.

The composite coating of the present invention adheres well to the magnet body, and since it has a structure made up of both inorganic and organic constituents, it provides an effective barrier against both inorganic and organic matter. In addition, glassy interface layers have barrier properties, too.

In a particularly preferred embodiment of the present invention, corrosion protection of the magnetic material is further enhanced by the shape of the magnet body being particularly adapted to allow the formation of a coating covering the magnet body with a uniform thickness. To this aim, the magnet body has no sharp edges, but rather rounded forms such as soft edges. Preferably, the magnet body is rod-shaped having a channel extending therethrough in a longitudinal direction for receiving the motor shaft of an intravascular blood pump, the opposing front faces of the magnet body being bevelled towards the channel. The channel does not need to be coated with the composite coating because in an intravascular blood pump the channel receives the motor shaft and is fixed thereto. Of course, the channel may be coated nevertheless, to be on the safe side.

The magnet body may be a single piece, or may be composed of several segments. In the latter case, each segment is provided with the inventive coating either surrounding it completely or at least the exposed surfaces thereof with a uniform thickness. Preferably, each segment has soft edges.

The present invention will be further explained with reference to the accompanying drawings, wherein FIG. 1 is a schematic longitudinal section of an exemplary embodiment of an intravascular blood pump, FIG. 2a is a schematic representation of an exemplary single-piece magnet according to the present invention, FIG. 2b is a partial sectional view showing a detail of the magnet illustrated in FIG. 2a, and FIG. 3 is a schematic top view of an exemplary segmented magnet according to the present invention.

The drawings are not to scale. They should not be construed as limiting the invention in any manner.

The intravascular blood pump 10 illustrated in FIG. 1 has been described above. The pump is conventional in construction, but comprises a corrosion resistant permanent magnet 1 according to the present invention. In the pump of FIG. 1, the magnet 1 is rod-shaped, the opposing front faces being flat and parallel to each other. While the composite coating according to the present invention may effectively protect a magnet body having sharp edges as illustrated in FIG. 1 against corrosion over an extended period of time, it is preferred in the present invention to use a magnet body having a shape as illustrated in FIGS. 2 and 3. The individual layers of the composite coating completely extend over each previously applied composite coating layer.

FIG. 2a shows a single-piece magnet 1 having a rod shape and a bore or channel extending therethrough in a longitudinal direction. During use of the magnet in an intravascular blood pump 10 as illustrated in FIG. 1, the channel receives the motor shaft 25. The opposing front faces 4 of the magnet are tapered towards the channel. The magnet 1 is provided with a composite coating according to the invention at the outer surfaces 2 exposed to the fluid flowing in gap 26 and the tapered front faces 4. The inner surfaces 3 adjacent to the motor shaft 25 may or may not be coated. Edge 5 at the transition between the outer surface 2 and the front surface 4, as well as edge 6 at the transition between front surface 4 and the inner surface 3, are coated. The edges are soft, thus facilitating the formation of a well-adhering uniform coating. "N" and "S" indicate the north pole and the south pole of the magnet.

FIG. 2b is a partial sectional view along the dash-dot line in FIG. 2a. FIG. 2b shows the region of the magnet within the loop in FIG. 2a. FIG. 2b clearly shows the soft edges 5, 6.

FIG. 3 shows a segmented magnet 7. The magnet illustrated in FIG. 3 has four segments 8, 8'. Segments 8, which are opposite to one another, have the same magnetic polarity, as indicated by "N" in the top view of FIG. 3, and segments 8', which are also opposite to one another, have the same magnetic polarity, as indicated by "S" in the top view of FIG. 3. As a result, adjacent segments 8, 8' have opposite magnetic polarity.

Segments 8, 8' have, analogously to the single-piece magnet shown in FIG. 2, inner surfaces, outer surfaces, opposing front faces, edges at the transition between the outer surfaces and the front surfaces, and edges at the transition between the front surfaces and the inner surfaces. Front faces are designated 4', and the edges are designated 5' and 6', respectively, in correspondence to the designations in FIG. 2. In addition, segments 8, 8' have side surfaces 9, 9', separated by gaps in the drawing. Of course, when the magnet is in use, side surfaces 9, 9' contact each other. All surfaces of each segment of the magnet may be completely covered by the inventive composite coating, but side surfaces 9, 9' which are not exo posed because they contact each other, and the inner surfaces which are not exposed because they contact the motor shaft, do not need to be coated. Preferably all edges of all segments are soft edges.

Table 1 illustrates the results of corrosion testing of niobium iron boron magnets coated with different coatings. Twelve identical cylindrical non-magnetized $Nd_2Fe_{14}B$ sintered magnet bodies having a length of 12 mm and a diameter of 2.8 mm were coated as described below, and subjected to corrosion testing in an aqueous solution containing 0.9 weight % sodium chloride at 60° C. Test specimens were inspected daily until day 60, and thereafter inspected once a week. Corrosion of the magnetic material results in lifting or deformation of the coating. Thus, lifting of the coating or formation of a bulge at a surface of a test specimen indicates corrosion of the magnetic material. Formation of a bulge having a height of 0.1 mm as well as lifting of the coating were defined as being indicative of magnet failure.

Test specimens were prepared in the following manner:

All specimens: Non-magnetized neodymium iron boron magnet bodies (with phosphate passivation as purchased) were cleaned with isopropanol and then dried in an air stream. Then, coatings were applied, and after application of the coatings, the coated magnets were subjected to magnetization in a magnetic field. Magnetizing the magnet bodies before applying the inventive composite coating is not appropriate. Coating thicknesses were about 7 μm for the aluminum layer, about 100 nm for the silane layer, and about 10 μm for the Parylene layer, where applicable.

Specimens 1 and 2: the dry magnet bodies were coated with aluminum by ion vapor deposition. Upon exposure to air, an aluminum oxide layer (native aluminum oxide layer) formed. Then, Parylene C was plasma coated thereon.

Specimens 3 and 4: the dry magnet bodies were coated with aluminum by ion vapor deposition. Upon exposure to air, a native aluminum oxide layer formed at the exposed surface of the aluminum layer. No further coating was applied.

Specimen 5: the dry magnet body was coated with aluminum by ion vapor deposition. Upon exposure to air, a native aluminum oxide layer formed. Then, 3-(trimethoxysilyl)propyl methacrylate (silane A-174) was applied by plasma coating, followed by application of Parylene F by plasma coating.

Specimens 6 and 7: the dry magnet bodies were coated with aluminum by ion vapor deposition. Upon exposure to air, a native aluminum oxide layer formed. Then, an alcoholic solution (water/ethanol; acetic acid to achieve a pH of about 5 to 6; concentration of silane about 1%; reaction time about 5 minutes) containing silane A-174 was applied, and the alcohol evaporated. Finally, Parylene C was applied by plasma coating.

Specimen 8: the dry magnet body was coated with aluminum by ion vapor deposition. Upon exposure to air, a native aluminum oxide layer formed. Then, silane A-174 was applied by plasma coating, followed by application of Parylene C by plasma coating.

Ion vapor deposition for specimen 1 to 8 was performed in argon gas at about $10^{-3}$ mbar at a potential of about 1000 volts and 1500 amperes DC. Generally, from about 400 to 1000 volts and from about 500 to 1500 amperes DC are suitable.

Specimens 9 and 10: the dry magnet bodies were coated with a copolymer of ethylene and chlorotrifluoroethylene by spray coating. The coated magnets were subjected to baking, and then cooled.

Specimens 11 and 12: the dry magnet bodies were spray coated with polyphenylene sulfide resin and baked at 135° C. for thirty minutes.

TABLE 1

| Specimen # | | Time t until failure | | |
|---|---|---|---|---|
| invention | comparative | t < 3 days | 3 days ≤ t < 1 month | t ≥ 6 months |
| | 1 | | x | |
| | 2 | | x | |
| | 3 | | x | |
| | 4 | | x | |
| | 5 | | x | |
| 6 | | | | x |
| 7 | | | | x |
| 8 | | | | x |
| | 9 | x | | |
| | 10 | x | | |
| | 11 | x | | |
| | 12 | x | | |

Test results of coated $Nd_2Fe_{14}B$ magnets in 0.9% NaCl solution at 60° C.

Magnet fails when coating lifts or buckling reaches 0.1 mm

Magnets pass the test when time until failure is at least 6 months (1 month=30 days)

A magnet is corrosion resistant in terms of this invention when it passes the test, i.e. time until failure is at least 180 days Specimen samples 9, 10, 11, and 12, each having a resin coating according to the to state of the art directly applied to the neodymium iron boron magnet body, failed within less than 3 days in sodium chloride solution at 60° C. Specimen samples 1 to 5 comprising protective aluminum/aluminum oxide layers survived for a longer time. Specimen samples 3 and 4 which were corrosion protected by aluminum/aluminum oxide layers without any additional protective layers failed within less than 1 month. The same result was achieved when a coating consisting of Parylene C was applied directly onto the aluminum oxide layer, i.e. without a silane based interface layer (specimen samples 1 and 2). Additionally, the same result was achieved when a silane based interface layer was present between the aluminum oxide layer and the Parylene layer, but the Parylene layer did not consist of Parylene C (specimen sample 5).

Specimen sample 8 had essentially the same coating composition as specimen sample 5, and the individual layers of the composite coating were applied in the same manner. However, in specimen sample 8 Parylene C was used rather than the Parylene F of specimen sample 5. Surprisingly, this slight modification had the consequence that specimen sample 8 did not fail even after 6 months, while specimen sample 5 already failed within less than 1 month.

The coating compositions of specimen samples 6 and 7 were identical to the coating composition of specimen sample 8. However, in specimen sample 8 the interface layer was applied by plasma coating, while in specimen samples 6 and 7 a wet process was used for applying the interface layer. As a result, specimen samples 6 and 7 were still without any sign of corrosion when the test was stopped after one year, while specimen sample 8 did not survive twelve months in a corrosive environment.

The above test results provide a clear indication that a neodymium iron boron permanent magnet having a composite coating comprising a metal layer, a linker layer and an outer layer formed from poly(2-chloro-p-xylylene) has excellent corrosion resistance even under aggressive conditions, and may be advantageously used in an intravascular blood pump.

The test results also indicate that the application method of the linker layer influences the corrosion resistance. A particularly excellent corrosion resistance was achieved when the linker layer was applied by a wet process.

In order to achieve optimum corrosion protection it is advisable to apply the inventive composite coating to the non-magnetized magnet bodies, and to magnetize the magnet bodies only after the coating is applied.

Specimen samples 6, 7 and 8 fulfilled both the above conditions. Non-magnetized magnet bodies were coated with the inventive composite coating, and magnetized after application of the complete composite coating. As a result, specimen samples 6, 7 and 8 did not show any coating lifting, and buckling was less than 0.1 mm in 0.9 weight % NaCl solution at 60° C. for at least 180 days. Therefore, specimen samples 6, 7 and 8 are corrosion resistant magnets.

The invention claimed is:

1. A corrosion resistant permanent magnet comprising:
a magnet body; and
a composite coating provided on and covering surfaces of the magnet body, the composite coating comprising
a metal layer on the magnet body,
optionally a metal oxide layer on the metal layer at the surface facing away from the magnet body,
a linker layer on the metal layer or the metal oxide layer, and
a layer formed from poly(2-chloro-p-xylylene) on the linker layer.

2. The corrosion resistant permanent magnet of claim 1, wherein the magnet body is a sintered magnet body.

3. The corrosion resistant permanent magnet of claim 1, wherein the magnet body comprises a rare earth metal.

4. The corrosion resistant permanent magnet of claim 3, wherein the rare earth metal is neodymium.

5. The corrosion resistant permanent magnet of claim 1, wherein the magnet body is a rare earth metal iron boron permanent magnet.

6. The corrosion resistant permanent magnet of claim 5, wherein the magnet body is a sintered magnet body having $Nd_2Fe_{14}B$ crystals and a neodymium iron boron material surrounding the $Nd_2Fe_{14}B$ crystals, said neodymium iron boron material being richer in neodymium than the $Nd_2Fe_{14}B$ crystals.

7. The corrosion resistant permanent magnet of claim 1, wherein the magnet body is rod-shaped with all edges being rounded.

8. The corrosion resistant permanent magnet of claim 1, wherein a linker forming the linker layer is selected from silanes, mercaptans, phosphines, disulfides, and silanes having a thiol, phosphine or disulfide group.

9. The corrosion resistant permanent magnet of claim 8, wherein the silanes are selected from trimethoxysilanes- and triethoxysilanes having an acryloyloxy or methacryloyloxy functional group and linkers having bis-trimethoxysilyl or bis-triethoxysilyl functional groups.

10. The corrosion resistant permanent magnet of claim 8, wherein the silanes comprise a hydride functional group.

11. The corrosion resistant permanent magnet of claim 8, wherein the linker is selected from 3-(2-pyridylethyl)thiopropyl trimethoxysilane, 3-(4-pyridylethyl)thiopropyl trimethoxysilane, 2-(diphenylphosphino)ethyl triethoxysilane, bis(2-methacryloyl)oxyethyldisulfide, and dihexadecyldisulfide.

12. The corrosion resistant permanent magnet of claim 1, wherein a metal of the metal layer is selected from aluminum, titanium, tantalum, niobium, zirconium, platinum, gold, and a metal alloys comprising at least one of: aluminum, titanium, tantalum, niobium, and zirconium.

13. The corrosion resistant permanent magnet of claim 1, wherein a metal of the metal layer is selected from aluminum, titanium, tantalum, niobium, zirconium and a metal alloys thereof, and a surface of the metal layer facing away from the magnet body is covered by an oxide layer formed by oxidation of the metal or the metal alloy.

14. The corrosion resistant permanent magnet of claim 1, wherein a metal of the metal layer is selected from platinum, titanium, and zirconium.

15. The corrosion resistant permanent magnet of claim 1, wherein a metal of the metal layer is gold.

16. The corrosion resistant permanent magnet of claim 1, wherein the composite coating completely extends over all surfaces of the magnet body.

17. The corrosion resistant permanent magnet of claim 1, wherein a thickness of the metal layer or a combined thicknesses of the metal layer and the metal oxide layer is in a range from 5 µm to 20 µm.

18. The corrosion resistant permanent magnet of claim 1, wherein a thickness of the linker layer is in a range from 20 nm to 150 nm.

19. The corrosion resistant permanent magnet of claim 1, wherein a thickness of the layer formed from poly(2-chloro-p-xylylene) is in a range from 5 µm to 20 µm.

20. The corrosion resistant permanent magnet of claim 1, wherein a thickness of the composite coating is no more than 200 µm.

21. The corrosion resistant permanent magnet of claim 1, wherein a thickness of the composite coating is no more than 50 µm.

22. A method for producing a corrosion resistant permanent magnet, the method comprising:
providing a non-magnetized magnet body;
forming a metal layer on surfaces of the non-magnetized magnet body;
forming a linker layer on the metal layer or on a metal oxide layer formed on the metal layer;
forming a layer of poly(2-chloro-p-xylylene) on the linker layer; and
magnetizing the non-magnetized magnet body.

23. The method of claim 22, wherein the non-magnetized magnet body is a sintered non-magnetized magnet body.

24. The method of claim 22, wherein the metal layer is formed by applying a metal by ion vapor deposition, plasma deposition, or atomic layer deposition.

25. The method of claim 22, wherein the metal layer is formed by applying a metal by galvanic deposition from an ionic liquid.

26. The method of claim 22, wherein a metal of the metal layer is selected from aluminum, titanium, tantalum, niobium, zirconium, platinum, gold, and a metal alloys comprising at least one of aluminum, titanium, tantalum, niobium and zirconium.

27. The method of claim 22, wherein the linker layer is formed by applying a linker by at least one of: physical vapor deposition using plasma, physical vapor deposition without using plasma, or a wet process.

28. The method of claim 27, wherein a linker forming the linker layer is selected from silanes; mercaptans; phosphines; disulfides; silanes having a thiol, phosphine or disulfide group; 3-(2-pyridylethyl)thiopropyl trimethoxysilane; 3-(4-pyridylethyl)thiopropyl trimethoxysilane, 2-(diphenylphosphino)ethyl triethoxysilane; bis(2-methacryloyl)oxyethyldisulfide; and dihexadecyldisulfide.

29. The method of claim 22, wherein the layer of poly (2-chloro-p-xylylene) is formed by plasma deposition of dichloro[2.2]paracyclophane.

30. The method of claim 22, wherein a thickness of the metal layer or a combined thicknesses of the metal layer and the metal oxide layer is in a range from 5 µm to 20 µm.

31. The method of claim 22, wherein a thickness of the linker layer is in a range from 20 μm to 150 μm.

32. The method of claim 22, wherein a thickness of the layer of poly(2-chloro-p-xylylene) is in a range from 5 μm to 20 μm.

33. The method of claim 22, wherein the metal layer, the linker layer, and the layer of poly(2-chloro-p-xylylene) together comprise a composite coating, and wherein a thickness of the composite coating is no more than 200 μm.

34. The method of claim 22, wherein the metal layer, the linker layer, and the layer of poly(2-chloro-p-xylylene) together comprise a composite coating, and wherein a thickness of the composite coating is no more than no more than 50 μm.

35. The method of claim 22, wherein the non-magnetized magnet body is a rare earth metal.

36. The method of claim 35, wherein the rare earth metal is neodymium.

37. The method of claim 22, wherein the non-magnetized magnet body is a rare earth metal iron boron permanent magnet.

38. The method of claim 37, wherein the non-magnetized magnet body is a sintered non-magnetized magnet body having $Nd_2Fe_{14}B$ crystals and a neodymium iron boron material surrounding the $Nd_2Fe_{14}B$ crystals, said neodymium iron boron material being richer in neodymium than the $Nd_2Fe_{14}B$ crystals.

39. The method of claim 22, wherein the non-magnetized magnet body is rod-shaped with all edges being rounded.

40. An intravascular blood pump comprising an electric motor, wherein the electric motor comprises a permanent magnet comprising:

a magnet body; and a composite coating provided on and covering surfaces of the magnet body, the composite coating comprising a metal layer on the magnet body, a linker layer on the metal layer, and a layer formed from poly(2-chloro-p-xylylene) on the linker layer.

* * * * *

UNITED STATES PATENT AND TRADEMARK OFFICE
CERTIFICATE OF CORRECTION

PATENT NO. : 11,107,626 B2
APPLICATION NO. : 16/346198
DATED : August 31, 2021
INVENTOR(S) : Thorsten Siess et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 105 days.

In the Specification

Column 2, Line 29:
Now reads: "(q=0.75"; should read -- (η=0.75 --

Column 5, Line 31:
Now reads: "poly(2-chloro-pxylylene),"; should read -- poly(2-chlor-p-xylylene), --

Column 6, Lines 4-5:
Now reads: "1-ethyl-3-methylimidazoliumchloride."; should read -- 1-ethyl-3-methylimidazolium-chloride. --

Column 8, Line 54:
Now reads: "R1 to R4"; should read -- $R^1$ to $R^4$ --

Column 8, Line 55:
Now reads: "R1 to R4"; should read -- $R^1$ to $R^4$ --

Column 8, Line 57:
Now reads: "R1 to R4"; should read -- $R^1$ to $R^4$ --

Column 8, Line 59:
Now reads: "R1 to R4"; should read -- $R^1$ to $R^4$ --

Signed and Sealed this
Fourteenth Day of June, 2022

Katherine Kelly Vidal
*Director of the United States Patent and Trademark Office*

CERTIFICATE OF CORRECTION (continued)
U.S. Pat. No. 11,107,626 B2

Column 9, Line 4:
Now reads: "R1 to R4"; should read -- $R^1$ to $R^4$ --

Column 10, Line 49:
Now reads: "exo posed"; should read -- exposed --

Column 12, Line 22:
Now reads: "to state"; should read -- state --

In the Claims

Column 13, Line 49, Claim 9:
Now reads: "linkers"; should read -- linker --

Column 13, Line 50, Claim 9:
Now reads: "groups"; should read -- group --

Column 13, Line 62, Claim 12:
Now reads: "alloys"; should read -- alloy --

Column 13, Line 67, Claim 13:
Now reads: "alloys"; should read -- alloy --

Column 14, Line 48, Claim 26:
Now reads: "alloys"; should read -- alloy --

Column 15, Line 13, Claim 34:
Now reads: "no more than no more than"; should read -- no more than --